(12) United States Patent
Muyari et al.

(10) Patent No.: US 8,226,544 B2
(45) Date of Patent: Jul. 24, 2012

(54) ENDOSCOPE TREATMENT TOOL

(75) Inventors: Yuta Muyari, Tokyo (JP); Naohisa Yahagi, Tokyo (JP)

(73) Assignees: Olympus Medical Systems Corp., Tokyo (JP); Naohisa Yahagi, Tokyo (JP)

( * ) Notice: Subject to any disclaimer, the term of this patent is extended or adjusted under 35 U.S.C. 154(b) by 927 days.

(21) Appl. No.: 12/098,064

(22) Filed: Apr. 4, 2008

(65) Prior Publication Data
US 2008/0249354 A1 Oct. 9, 2008

(30) Foreign Application Priority Data

Apr. 6, 2007 (JP) ................ P2007-100306

(51) Int. Cl.
*A61B 1/00* (2006.01)
(52) U.S. Cl. ........ 600/107; 600/104; 600/106; 600/127; 600/129
(58) Field of Classification Search ............... 600/104, 600/106–107, 127, 129
See application file for complete search history.

(56) References Cited

U.S. PATENT DOCUMENTS

| | | | | |
|---|---|---|---|---|
| 4,245,624 | A * | 1/1981 | Komiya | 600/106 |
| 4,401,123 | A * | 8/1983 | Baba | 600/462 |
| 4,763,662 | A * | 8/1988 | Yokoi | 600/461 |
| 6,824,509 | B2 * | 11/2004 | Yamaya et al. | 600/106 |
| 7,060,024 | B2 * | 6/2006 | Long et al. | 600/106 |
| 7,566,300 | B2 * | 7/2009 | Devierre et al. | 600/104 |
| 2001/0049509 | A1 | 12/2001 | Sekine et al. | |
| 2003/0176766 | A1 * | 9/2003 | Long et al. | 600/106 |
| 2004/0158127 | A1 | 8/2004 | Okada et al. | |
| 2004/0225305 | A1 | 11/2004 | Ewers et al. | |
| 2005/0234296 | A1 * | 10/2005 | Saadat et al. | 600/129 |

FOREIGN PATENT DOCUMENTS

| | | |
|---|---|---|
| EP | 0 076 525 A1 | 4/1983 |
| JP | 2003-210389 A | 7/2003 |
| JP | 2003-310545 A | 11/2003 |
| JP | 2004-261372 | 9/2004 |
| JP | 2006-296488 A | 11/2006 |
| KR | 10-0685337 | 7/2005 |
| KR | 10-2006-0101521 | 9/2006 |
| WO | WO 2005/058239 A2 | 6/2005 |

OTHER PUBLICATIONS

Office Action (Notice of Allowance) dated Dec. 10, 2010 received from the Korean Intellectual Property Office.
Japanese Office Action dated Nov. 15, 2011 from corresponding Japanese Patent Application No. JP 2007-100306, together with partial English language translation.

* cited by examiner

*Primary Examiner* — Matthew J Kasztejna
(74) *Attorney, Agent, or Firm* — Scully, Scott, Murphy & Presser, P.C.

(57) ABSTRACT

The endoscope treatment tool 1 has a distal end member 3 which is installed in an endoscope. A connection member 4 is attached to the distal end member 3 in a freely rotatable manner. In the connection member 4, a portion which is supported by a cap 12 of the distal end member 3 is a second pivot shaft 15. A portion penetrating a supporting member 21 of a treatment portion 5 is a first pivot shaft 23. The first pivot shaft 23 is also a rotational axis of a pair of forceps members 22 provided in the treatment member 5. When the forceps members 22 are used, a coil sheath 6 is extended by an operation at the side of the proximal end. The connection member 4 rotates about the second pivot shaft 15, which is a fulcrum, and the treatment portion 5 moves forward beyond the cap 12. In accordance with the present invention, it is possible to resolve the difficulty of procedures by positioning the treatment portion in an appropriate location.

7 Claims, 8 Drawing Sheets

ENDOSCOPE TREATMENT TOOL

BACKGROUND OF THE INVENTION

1. Field of the Invention

The present invention relates to an endoscope treatment tool that is used with an endoscope.

Priority is claimed on Japanese Patent Application No. 2007-100306, filed Apr. 6, 2007, the content of which is incorporated herein by reference.

2. Description of Related Art

An Endoscopic Mucosal Resection (EMR), which endoscopically resects a pathological lesion portion, has been conventionally used as a general medical treatment to a pathological lesion on an alimentary canal. Especially, an Endoscopic Submucosal Dissection (ESD) is a method to resect the pathological lesion portion by dissecting a submucosal layer after cutting out a mucous membrane around the pathological lesion portion which is known to be a reliable endoscopic medical treatment which is able to collectively resect the pathological lesion portion.

When the above-mentioned ESD is performed, the pathological lesion portion is distended by injecting a physiologic saline solution or the like into a normal mucous membrane around the pathological lesion portion using an injection needle, a boundary between the pathological lesion portion and the normal mucous membrane is resected by using a high-frequency cutting instrument such as a high-frequency knife, a snare, or the like (for example, see Patent Document 1). At this time, submucosal layer dissection is proceeded by lifting the pathological lesion portion to a high enough position to assure enough of the portion to be resected on the boundary between the pathological lesion portion and the normal mucous membrane or by lifting the mucous membrane by inserting a transparent cap installed at the distal end of the endoscope under the mucous membrane to have enough portion to be resected when the pathological lesion portion is a flat shape.

Patent Document 1: Japanese Unexamined Patent Application, First Publication No. 2004-261372

SUMMARY OF THE INVENTION

A first aspect of the present invention is an endoscope treatment tool consists of a cylindrical distal end member provided at the distal end of an endoscope, a treatment portion for performing a treatment to a biological tissue, an insertion portion provided in the axial line direction of the endoscope so as to freely extend and retract and the treatment portion is fixed at the distal end thereof, a connection member for respectively connecting the treatment portion and the distal end member in a freely rotatable manner, a first pivot shaft for connecting the connection member and the treatment portion so as to freely rotate, a second pivot shaft for connecting the connection member and the distal end member so as to freely rotate, in which the second pivot shaft is disposed so as to be able to rotate the connection member so that the first pivot shaft is moved from a location which is proximal to the second pivot shaft and the lateral side of the distal end member to a location which is distal to the second pivot shaft.

A second aspect of the present invention is the endoscope treatment tool in accordance with the first aspect, wherein the distal end member is a cap which is freely attached and detached to the endoscope.

A third aspect of the present invention is the endoscope treatment tool in accordance with the second aspect, wherein the connection member rotates when the insertion portion is extended or retracted relative to the endoscope, and when the insertion portion is extended relative to the endoscope, the first pivot shaft moves from a location proximal to the second pivot shaft to a location distal to the second pivot shaft.

A fourth aspect of the present invention is the endoscope treatment tool in accordance with the third aspect, wherein the distance between the treatment portion and the endoscope is maximized when the connection portion rotates and the first pivot shaft and the second pivot shaft are disposed on an identical plane which is substantially perpendicular to the longitudinal direction of the distal end member.

A fifth aspect of the present invention is the endoscope treatment tool in accordance with the fourth aspect, wherein when the connection member rotates and the first pivot shaft moves distal to the distal end surface of the distal end member, the treatment portion projects from a distal end surface of the endoscope.

A sixth aspect of the present invention is the endoscope treatment tool in accordance with the fourth aspect, wherein the connection member rotates and the first pivot shaft is moved distal to the distal end surface of the distal end member, the treatment portion is moved to a place beyond the center line of the distal end member.

A seventh aspect of the present invention is the endoscope treatment tool in accordance with any one of the first aspect to the sixth aspect, wherein the treatment portion is provided with a constitution in which a pair of forceps members is supported by a supporting member so as to be freely opened and closed, and each of the forceps members is supported by the supporting member and the first pivot shaft.

An eighth aspect the present invention is the endoscope treatment tool in accordance with the seventh aspect, wherein the second pivot shaft is coaxially inserted into each of a pair of holes formed in the distal end member, and the connection member is curved so as to follow the outer shape of the distal end member.

DETAILED DESCRIPTION OF THE INVENTION

The best embodiment for carrying out the present invention shall be described in detail with reference to figures.

Figure 1:
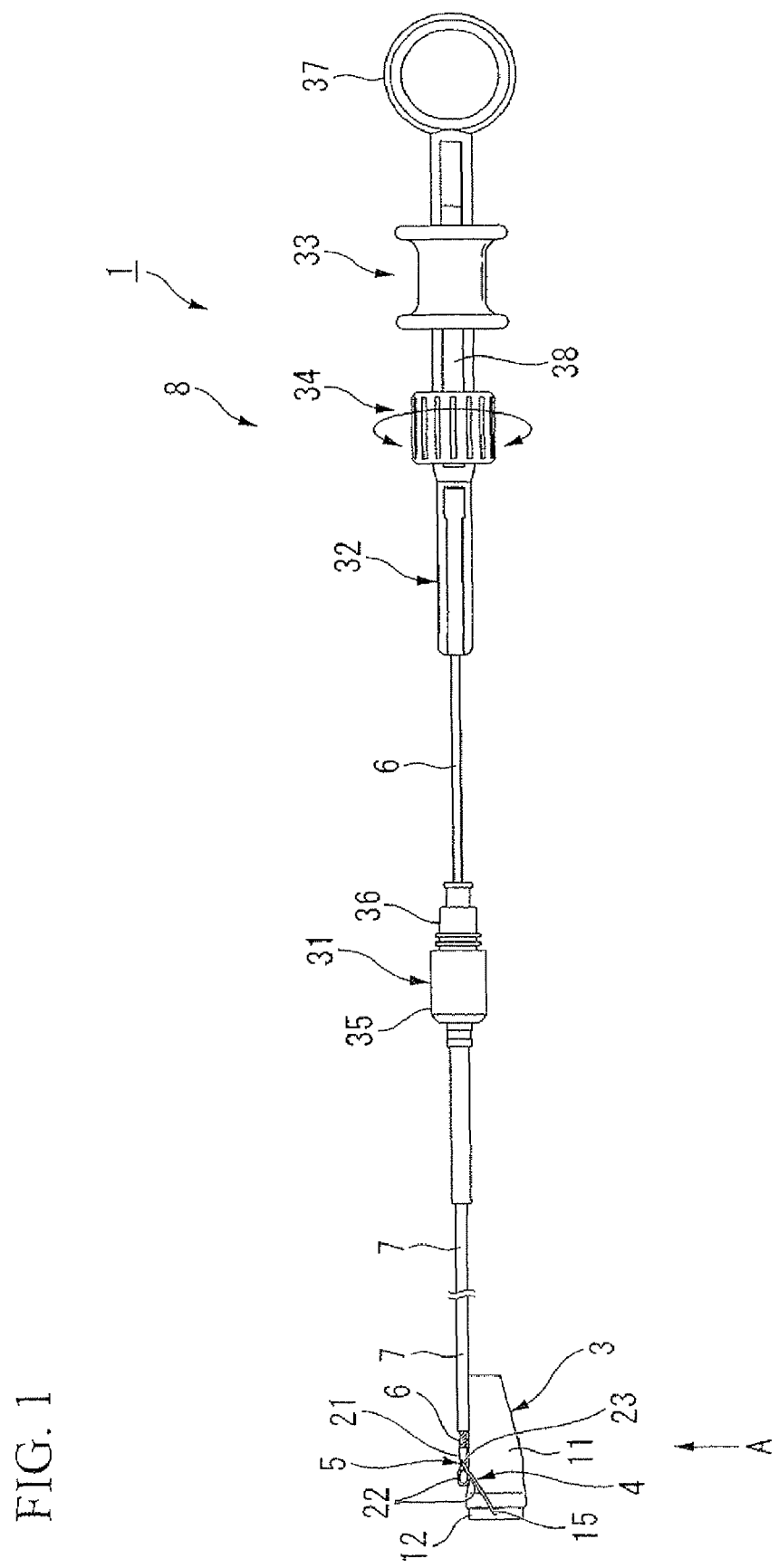
FIG. 1 shows an endoscope treatment tool.

As shown in FIG. 1, an endoscope treatment tool 1 consists of a distal end member 3 installed at the distal end of an endoscope, a treatment portion 5 connected to the distal end member 3 via a connection member 4, an elongated coil sheath 6 to which the treatment portion 5 is fixed, an external tube 7 through which the coil sheath 6 is passed so as to freely extend or retract, an operation portion 8 provided at the side of the proximal end which is the proximal side of the operator for operating the treatment portion 5.

Figure 2:
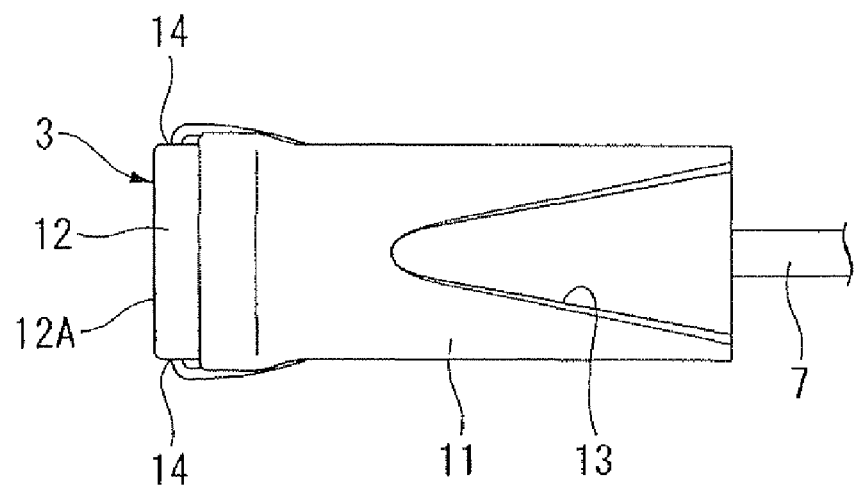
FIG. 2 is a view from the direction of arrow A of FIG. 1.
Figure 3:
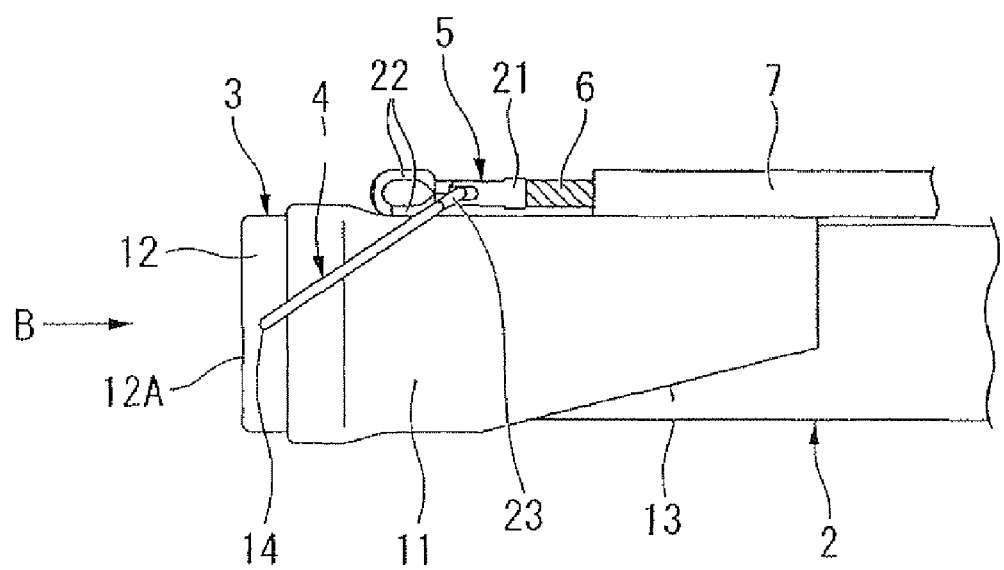
FIG. 3 shows a distal end member installed in the endoscope and geometry of a treatment portion.

As shown in FIGS. 2 and 3, the distal end portion 3 consists of a hood 11 which is installed at the distal end of the endoscope 2, and a cylindrical cap 12 which is integrally provided with the hood 11. In the hood 11, a slit 13 is provided in parallel with a longitudinal direction from a side proximal to the cylinder thereof. The hood 11 is made of a flexible material so as to be easily installed in the endoscope 2. The cap 12 has a cylindrical shape and its inner diameter is greater than the outer diameter of the endoscope 2. The cap 12 is made of a hard and transparent material. In this embodiment, a distal end opening 12A of the cap 12 is disposed distal to the distal end surface of the endoscope 2. The opening 12A is formed substantially in parallel with the distal end surface of the endoscope 2.

Figure 4:
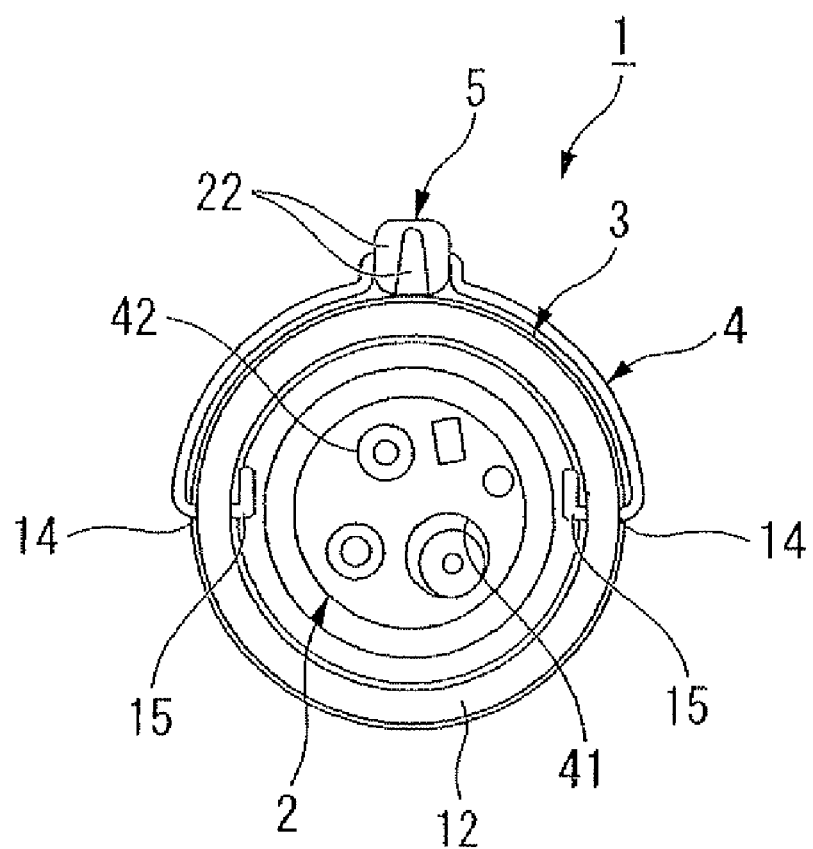
FIG. 4 is a view from the direction of arrow B of FIG. 3.
Figure 5:
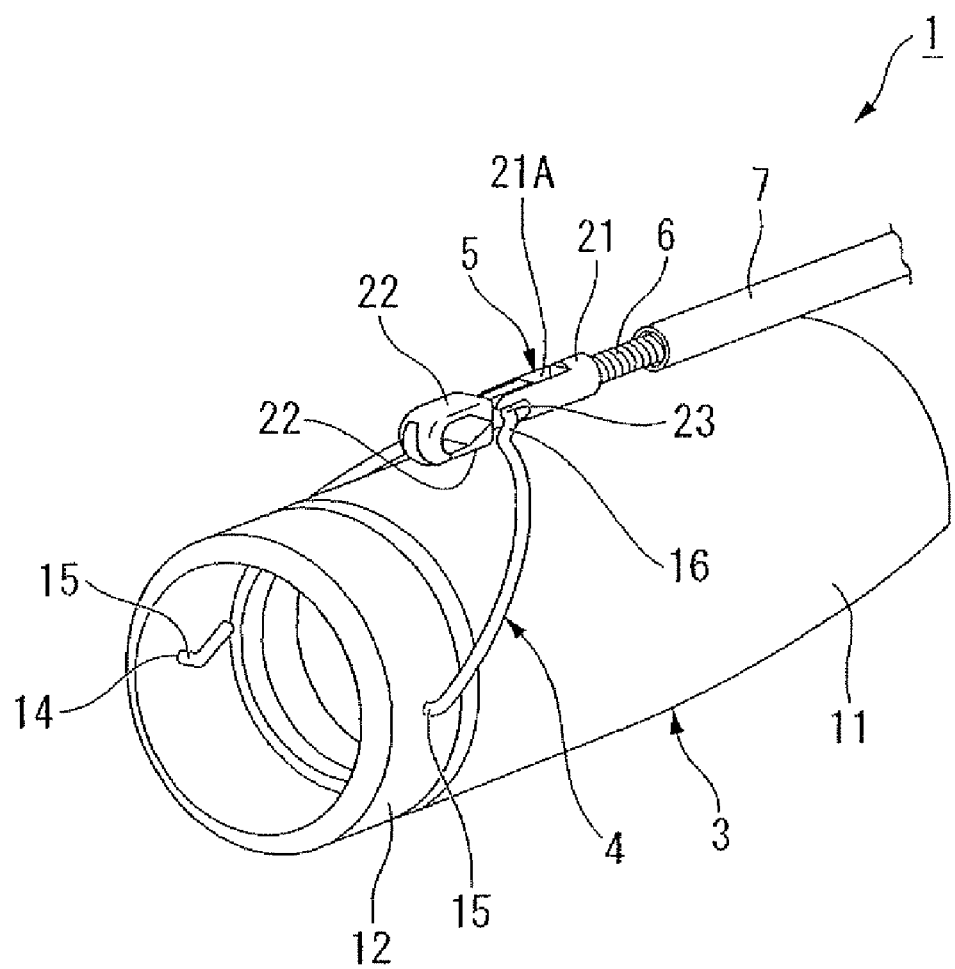
FIG. 5 is a perspective view that shows the distal end member and the treatment portion.

As shown in FIGS. 4 and 5, the connection member 4 is formed by forming a hard wire. Both end portions of the wire are respectively inserted into a pair of holes 14 which is formed in a diameter of the cap 12. The pair of holes 14 is disposed substantially 90 degrees shifted respectively on the circumference of the distal end member 3 relative to a location where the slit 13 of the hood 11 is formed. The axial line of the pair of holes is perpendicular to the longitudinal direction of the distal end member 3. Both end portions of the connection member 4 are inserted into each of the pair of holes 14 from the outer side through to the inner side one by one and are folded back at the cap 12 so as to prevent them from falling out. In the connection member 4, the portions inserted into the holes 14 become a second pivot shaft 15 for performing an operation which is to be hereinafter described. The second pivot shaft 15 is inserted into each of the pair of holes 14 in parallel to the axial line of the hole 14. The second pivot shaft 15 is disposed coaxially. Since the second pivot shaft 15 does not penetrate the distal end member 3 as a whole, it does not interrupt the field of view of the endoscope 2 or the operations of the treatment instrument which is passed through the operation channel.

The connection member 4 is extracted from each of the pair of holes 14 and is extended toward the treatment portion 5 by being curved so as to follow the outer shape of the distal end member 3 and penetrates a supporting member 21 which forms the treatment portion 5. A portion 16 in the vicinity of the supporting member 21 is bent so as to surround the supporting member 21. Here, the connection member 4 is curved so as to follow the outer shape of the distal end member 3 in a way from the cap 12 to the portion of the side of the supporting member 21. However, the connection member 4 may be bent in more than one portion on both sides of the distal end member 3.

The treatment portion 5 is fixed to the supporting member 21 so as to make a pair of forceps members 22 freely open or close. In the side of the distal end of the forceps members 22, a portion for grasping a biological tissue is provided and it is connected to the inside of the slit 21A of the supporting member 21 and further the proximal end thereof is connected to an operation wire which is not shown. The connection member 4 penetrates between the portion for grasping a biological tissue and a connection portion connected to the operation wire. The connection member 4 is supported by the supporting member 21 in a freely rotatable manner with the connection member 4 as a rotational axis. A portion of the connection member 4 which is penetrating the supporting member 21 is a first pivot shaft 23. The first pivot shaft 23 is disposed in parallel with the second pivot shaft 15. The first pivot shaft 23 is disposed in a position which is shifted 90 degrees from each of the pair of the second pivot shafts 15 with the axial line of the distal end member 3 as the center. Therefore, an imaginary line passing the axial line of the distal end member 3 which is identical to the first pivot line 23 and the center of the treatment portion 5 and an imaginary line passing the center of the distal end member 3 which is the axial line of the second pivot shaft 15 intersects at right angles. The operation wire is connected to the operation portion 8 by passing through the inside of the coil sheath 6.

The coil sheath 6 is formed to have flexibility by closely winding the wire. At the distal end of the coil sheath 6, a supporting member 21 of the treatment portion 5 is fixed. At the proximal end which is the side of the proximal end of the operator, the operation portion 8 is fixed. The length of the coil sheath 6 is longer than the external tube 7. Both sides which are distal to and proximal to the coil sheath 6 are respectively exposed from the external tube 7.

The external tube 7 has flexibility. The distal end portion of the external tube 7 is adhesively fixed to the hood 11. The external tube 7 is adhered to the hood 11 at substantially opposite side from the slit 13 which is a place shifted respectively by 90 degrees on the circumference of the distal end member 3 from locations where the pair of holes 14 for supporting the connection member 4 is formed.

The operation portion 8 consists of a first lock mechanism which switches between engagement and disengagement between the external tube 7 and the coil sheath 6, an operation main body 32 to which the coil sheath 6 is fixed, a slider 33 which is freely extendable and retractable relative to the operation main body 32, a second lock mechanism 34 which controls the movement of the slider 33.

The first lock mechanism 31 consists of a base member 35 which is fixed to the external tube 7 and an engagement member 36 which is able to be engaged and disengaged with the base member 35. The coil sheath 6 is fixed to the engagement member 36. When the engagement member 36 is engaged with the base member 35, the coil sheath 6 is fixed relative to the external tube 7 and so a relative rotation, extension, or retraction is not possible. When the engagement member 36 is disengaged with the base member 35, the coil sheath 6 can extend or retract relative to the external tube 7.

The coil sheath 6 is fixed to the inside of the distal end of the operation main body 32. A ring 37 for holding onto is provided on the side of the proximal end of the operation main body 32. A slit 38 is provided in parallel with the longitudinal direction on the side distal to the ring 37. In this slit 38, a slider 33 is fixed so as to freely extend and retract in the longitudinal direction. The operation wire, which is extracted from the coil sheath 6, is fixed to the slider 33. In a position which is distal to the slider 33 within the range of movement of the slider 33, the second lock mechanism 34 is disposed. The second lock mechanism 34 is movable along the slit 38 and is provided with a mechanism which locks itself at its location by rotating itself in the direction shown by the arrow. One example of this kind of mechanism is one in which a tightening member for controlling the movement of the slide member by tightening is provided in a rotatable manner on the outer circumference of the slide member which moves along the slit 38.

Next, operations of the endoscope treatment tool 1 in accordance with the present embodiment will be described by taking a case, in which an ESD procedure is performed, as an example.

First, the hood 11 of the endoscope treatment tool 1 is installed in the distal end portion of the endoscope 2. At this time, as shown in FIG. 4, positional adjustment is made so that the treatment portion 5 is located distant from the operation channel 41 of the endoscope 2. In this kind of positioning, an observation device 42 is positioned on the side of the treatment portion 5. The external tube 7 is fixed relative to the endoscope 2 via the hood 11 and so the external tube 7 and the coil sheath 6 get treated substantially along the endoscope 2. When the coil sheath 6 is extracted relative to the external tube 7 by unlocking the first lock mechanism 31 at the side of the operation portion 8, the connection member 4 is disposed in a position, in which the first pivot shaft 23 is more proximal than the second pivot shaft 15, and on the side surface of the distal end member 3. Since the connection member 3 is formed to follow the outer shape of the distal end member 3, the outer size of the endoscope treatment tool 1 as a whole does not become large.

Figure 6:
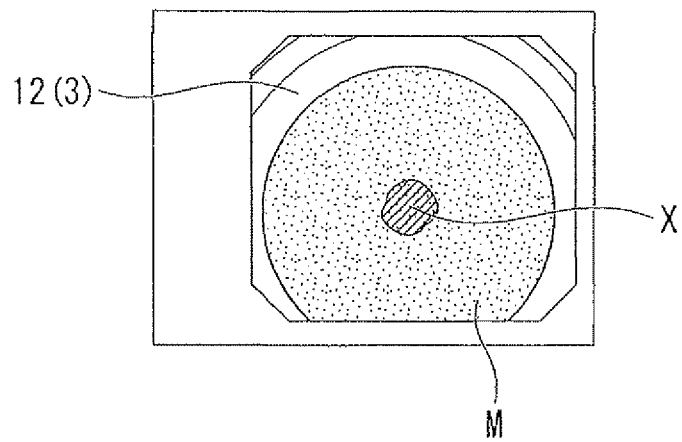
FIG. 6 shows one example of an endoscopic image.

When the distal end member 3 is installed, the endoscope treatment tool 1 and the endoscope 2 are inserted to a vicinity of the pathological lesion portion which is an object portion from the mouth of a patient which is a natural opening. The pathological lesion portion can be confirmed by images obtained by the observation device 42 provided at the distal end of the endoscope 2. As shown in FIG. 6, one example of the endoscopic image, the cap 12, appears only in the peripheral portion, but the cap 12 doesn't appear in the center portion which faces the pathological lesion portion X. Since the cap 12 is made of a member which is transparent relative to the observation device 42, images inside of the body can be confirmed through the cap 12. At this stage, the treatment portion 5 does not appear in the field of view.

Observation is performed by the endoscopic images, and the orientation of the endoscope 2 is adjusted so that the operation channel 41 of the endoscope 2 moves proximal to and the treatment portion 5 of the endoscope treatment tool 1 moves distal to relative to the pathological lesion portion X, an injection needle which is not shown is passed through the operation channel 41. The injection needle is inserted from the side proximal to the pathological lesion portion X to the submucosal layer, a physiologic saline solution is injected to the submucosal layer so that the pathological lesion portion X is distended.

Figure 7:
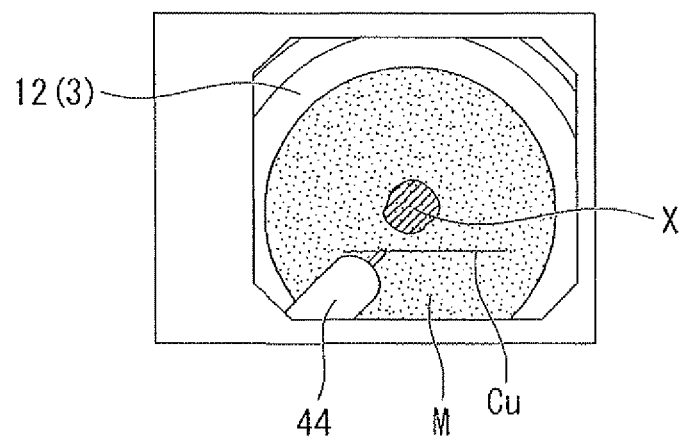
FIG. 7 shows one example of an endoscopic image when a procedure is performed using a high-frequency knife.

Next, as disclosed in Patent Document 1 for example, a high-frequency knife is inserted endoscopically to perform an initial cut by opening a hole in a part of a mucous membrane M around the pathological lesion portion X. Furthermore, as shown in FIG. 7, by confirming with the endoscopic images, high frequent electrical current is applied and the high-frequency knife 44 is moved to enlarge the hole for the initial cut to a predetermined size. In this way, the submucosal layer is cut and dissected from a wound Cu formed on the mucous membrane M in the vicinity of the pathological lesion portion X.

At this time, when the coil sheath 6 is extended by holding the base member 35 of the first lock mechanism 31, the connection member 4 rotates as the second pivot shaft 15 a fulcrum. The first pivot shaft 23 moves along an arc, the center of which is the second pivot shaft 15. As a result, the treatment portion 5 which is connected by the first pivot shaft 23 of the connection member 4 is extracted along a trajectory of the first pivot shaft 23. That is, a linear movement of the coil sheath 6 is converted to a movement along the arc of the treatment portion 5 by the connection member 4. This treatment portion 5 extends by moving away from the distal end member 3 from the housing position which is an initial state. The treatment portion 5 is most distant from the distal end member 3 at a position where the first pivot shaft 23 and the second pivot shaft 15 are on a surface which is perpendicular to the longitudinal direction of the distal end member 3. After that, when the first pivot shaft 23 moves to the side distal to the second pivot shaft 15, the treatment portion 5 advances toward the wound Cu beyond the center axis of the distal end member 3.

Figure 8:
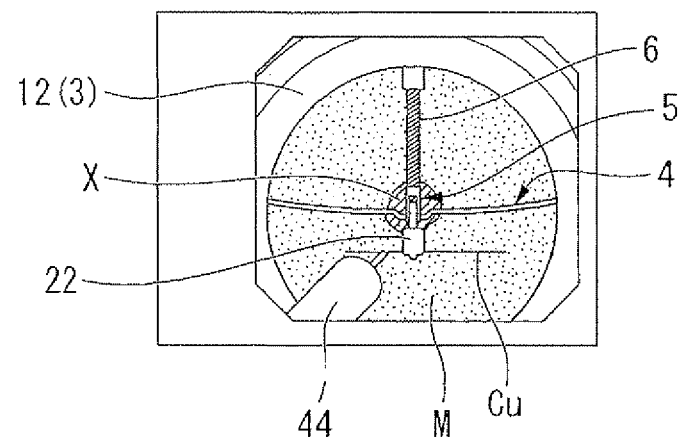
FIG. 8 shows one example of an endoscopic image when a connection portion is rotated and the treatment portion is moved toward a biological tissue.

As shown in FIG. 8, since the treatment portion 5 can be confirmed with the endoscopic image, when the pair of forceps members 22 reaches the wound Cu, the advancement of the coil sheath 6 is stopped. At this position, when the engagement member 36 of the first lock mechanism is twisted to be engaged with the base member 35, the coil sheath 6 is fixed to the external tube 7.

Furthermore, the biological tissue on the side of the pathological lesion portion X of the wound Cu is captured by extending and retracting the slider 33 and opening and closing the pair of forceps members 22. The outer circumference portion of the second lock mechanism 34 is rotated at a state in which the second lock mechanism 34 is in contact with the slider 33, and the slider 33 is fixed relative to the operation main body 32. Since the slider 33 is not allowed to move in the proximal direction, even when the hand of the operator is released from the slider 33, the pair of forceps members 22 does not open and so the biological tissue is prevented from being fallen down.

Figure 9:
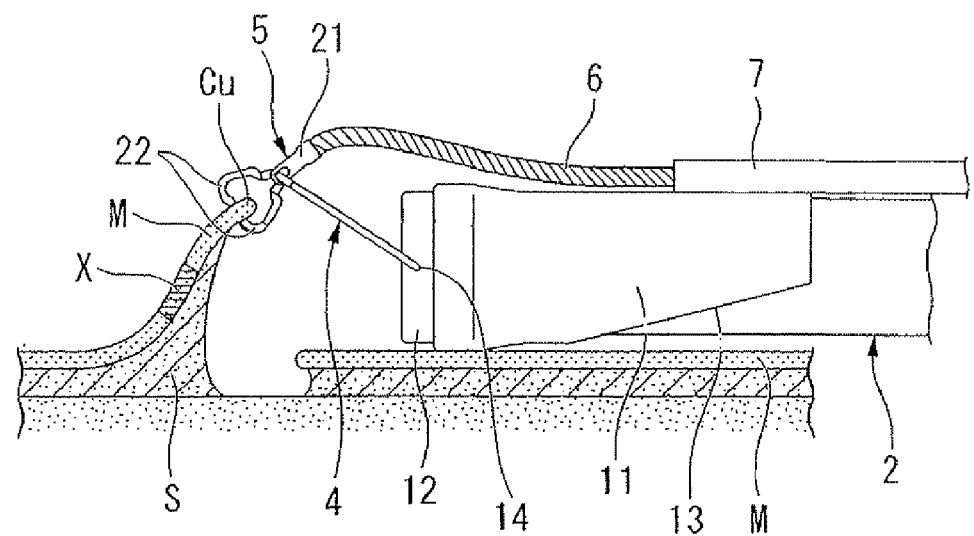
FIG. 9 shows a state when the biological tissue is lifted by the treatment portion.
Figure 10:
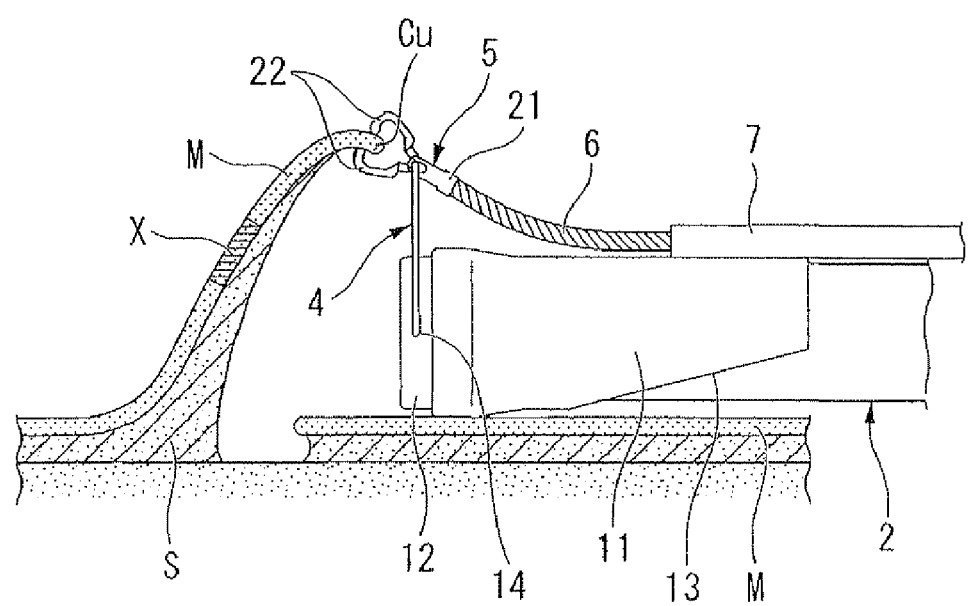
FIG. 10 shows a state when the biological tissue is lifted to the highest position.

Furthermore, the engagement of the first lock mechanism 31 is released, the coil sheath 6 is retracted relative to the external tube 7. As shown in FIG. 9, the connection member 4 rotates about the second pivot shaft 15 and the treatment portion 5 is retracted to the side of the proximal end which is a direction away from the pathological lesion portion X. The biological tissue around the wound Cu is lifted and the mucous membrane M is lifted. Since the front field of view is assured, the submucosal layer is cut out and dissected by the high-frequency knife 44. After a predetermined length is cut, the above-mentioned operations are repeated and the cut is proceeded while grasping the wound Cu of the mucous membrane M by the pair of forceps members 22. As shown in FIG. 10, by retracting the coil sheath 6 to a position where the first pivot shaft 23 is in line with the second pivot shaft 15 on the identical surface which is perpendicular to the longitudinal direction of the distal end member 3, it is possible to lift the biological tissue to a position farther away from the endoscope 2 and the distal end member 3. After resecting all the biological tissue around the pathological lesion portion X, this pathological lesion portion X is grasped by a forceps member (not shown) and is endoscopically extracted and then the treatment is finished.

In accordance with this embodiment, since it is possible to move the treatment portion 5 by the connection member 4, it is possible to move the treatment portion to a position for facilitating the procedure or for assuring the field of view while grasping the mucous membrane M even when the cut is proceeding. Therefore, the procedure is further aided by making it unnecessary to grasp the mucous membrane M again by the treatment portion 5 when the cut is proceeding. Also, when the cut is proceeding, it is possible to apply appropriate tension to the submucosal layer S, putting it into a state in which it is easily cut.

Since the supporting member 21 and the coil sheath 6 are made so as to be able to extend and retract relative to the distal end member 3, it is possible to easily approach the mucous membrane M.

Since the treatment portion 5 is connected to the connection member 4 which rotates about the second pivot shaft 15 as a fulcrum, it is possible to move the treatment portion 5 within a wide range along the distal end member 3 from the housing position to a position where the biological tissue is grasped. Since it is possible to move the treatment portion 5 only by extending and retracting operations of the coil sheath 6, the operation is easy. In the housing position, since it is possible to form an outer shape including the endoscope 2 as a whole small, it is possible to suppress friction during the insertion to the body. Since the position where the biological tissue is grasped is set in a protruding position which is beyond the respective center axes of the distal end member 3 and the endoscope 2 toward the biological tissue, the biological tissue is easily grasped. At the position where the treatment portion 5 is most distant from the distal end member 3, it is possible to lift the biological tissue to a height higher than the diameters of the endoscope 2 and the distal end member 3, making the procedure easy. Since the biological tissue is lifted to this height, it is possible to cut out a wide segment and so it is possible to reduce the difficulty stemming from grasping the mucous membrane M again.

Further in accordance with the present embodiment, the pair of forceps members 22 is the first pivot shaft 23, it is possible to downsize the treatment portion 5 and to reduce the number of components. Since a part of the wire surrounding the supporting member 21, which is the first pivot shaft 23, is bent, it is possible to prevent dislocation in the axial line direction.

Since the external tube 7 is fixed to the hood 11, it is possible to make the external tube 7 and the coil sheath 6 not easily separated from the endoscope 2, and so facilitates its insertion into the body.

Since the first lock mechanism 31 is provided in the operation portion 8, it is possible to fix the coil sheath 6 to the external tube 7, and it is easy to maintain the position of the treatment portion 5. Since the second lock mechanism 34 for fixing the slider 33 is provided, it is easy to maintain a state in which the biological tissue is grasped by the pair of forceps members 22. Due to this, the difficulty of operations is resolved.

Alternative examples of the second lock mechanism for fixing the slider by the operation portion are shown in FIG. 11 to FIG. 14.

Figure 11:
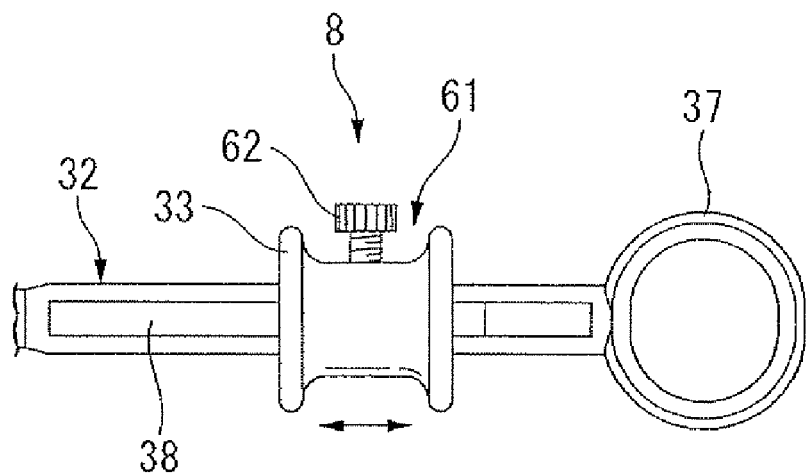
FIG. 11 shows an alternative example of a second lock mechanism.

A second lock mechanism 61 shown in FIG. 11 is made of a screw 62 which is threaded into the slider 33. A threaded hole formed in the slider 33 opens toward the operation main body 32. When the screw 62 is tightened, the slider 33 can be fixed to the operation main body 32. When the screw 62 is loosened, the slide 33 can be extended and retracted relative to the operation main body 32.

Figure 12:
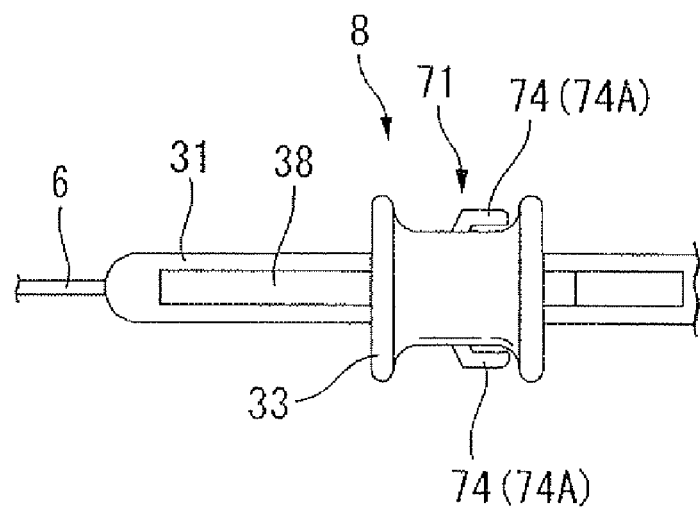
FIG. 12 shows an alternative example of a second lock mechanism.
Figure 13:
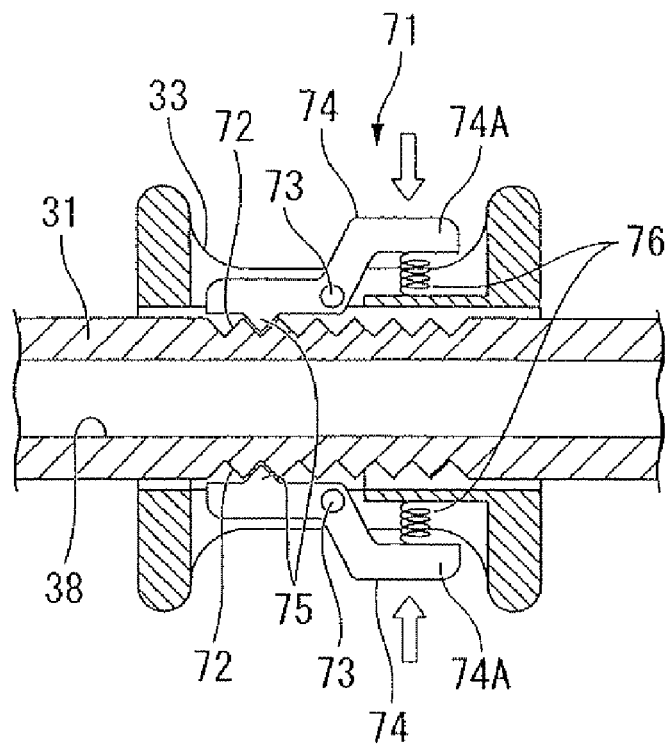
FIG. 13 is a sectional view that shows a constitution of the second lock mechanism shown in FIG. 12.
Figure 14:
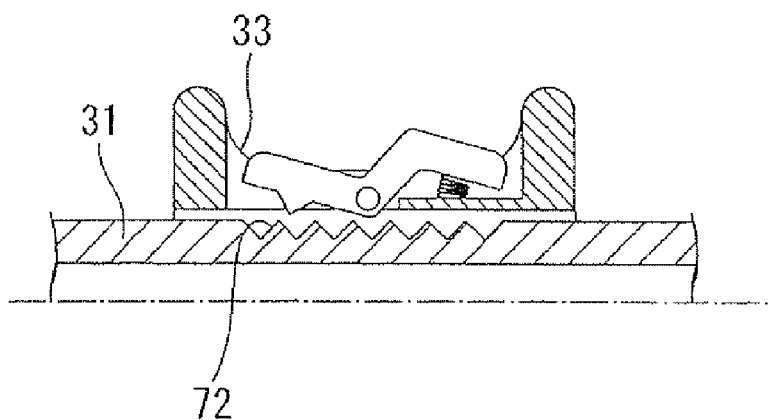
FIG. 14 shows a state when an engagement between a ratchet claw and ratchet teeth by pushing a lever.

A second lock mechanism 71 shown in FIGS. 12 and 13 uses a ratchet mechanism. The second lock mechanism 71 consists of a ratchet tooth 72 plurally arranged in the longitudinal direction of the operation body 32 and a ratchet claw 75 provided in the lever 74 which is supported by the pin 73 to the slider 33. The lever 74 is biased to a direction in which the ratchet claw 75 engages ratchet tooth 72. A lever end portion 74A which is the side of the lever connected to the coil spring 76, is projecting from the outer circumference of the slider 33. When the slider 33 is extended and retracted, the slider is grasped so as to push the lever end portion 74A. A pair of levers 74 rotates about the pin 73 and the engagement between the ratchet claw 75 and the ratchet tooth 72 is released. When the hand is released, the coil spring 76 is restored and the lever end portion 74A is projected and the ratchet claw 75 is engaged with the ratchet tooth 72 and so the slider 33 is fixed.

The present invention is not limited to the above-mentioned embodiments but can be widely applied.

For example, the second pivot shaft 15 may only be formed by one end portion of the wire of the connection member 4. The treatment portion 5 is cantilevered relative to the distal end member 3.

The pin may be provided in a location different from the first pivot shaft 23 in the treatment portion 5. The pair of forceps members 22 may be supported in a freely rotatable manner by the pin.

The external tube 7 may not be fixed to the hood 11. In this case, the external tube 7 is fixed to the endoscope 2 by a band or the like.

The endoscope treatment tool 1 may be constituted so that a high-frequency current can be applied. In this case, a terminal is provided in the slider 33 for connecting a high-frequency power source and the operation wire. The coil sheath 6 is covered by an insulating tube. It is possible to open a hole for starting a cut in the biological tissue by the treatment portion 5 or it is possible to stop bleeding from continuing.

The usage of the endoscope treatment tool 1 is not limited to a resection of the pathological lesion portion formed in the mucous membrane but may be used in other procedures. The treatment portion 5 is not limited to a type provided with a pair of forceps members which is freely opened and closed but may be other structures such as a snare.

In the endoscope treatment tool in accordance with the first aspect of the present invention, when the first pivot shaft is disposed proximal to the second pivot shaft, that is the side of the proximal end of the operator, the treatment portion is adjacently located on the lateral side of the distal end member. The distal end member is installed in the endoscope in this state and inserted into the body. When the treatment portion is used, the second pivot shaft is rotated and the connection member is rotated toward the side of the distal end. The treatment portion connected via the first pivot shaft is moved distal to and beyond the second pivot shaft which is a place where the biological tissue can be treated.

In the endoscope treatment tool in accordance with the second aspect of the present invention, it is possible to integrally treat the cap with the endoscope by installing the cap to the endoscope. By detaching the cap, it is possible to use the endoscope alone.

In the endoscope treatment tool in accordance with the third aspect of the present invention, it is possible to rotate the connection member about the second pivot shaft by extending or retracting the insertion portion. Therefore, it is possible to operate the position of the treatment portion by operating at the side of the proximal end.

In the endoscope treatment tool in accordance with the fourth aspect of the present invention, it is possible to move the treatment portion away from the endoscope farther than the case in which the treatment portion is extended or retracted along the endoscope.

In the endoscope treatment tool in accordance with the fifth aspect of the present invention, it is possible to move the treatment portion to a position projecting distal to the distal end member by rotating the connection member, whereby the procedure becomes easy.

In the endoscope treatment tool in accordance with the sixth aspect of the present invention, since it is possible to move the treatment portion beyond the center line of the distal end member, it is possible to perform a treatment relative to a biological tissue opposing a default position across the center line.

In the endoscope treatment tool in accordance with the seventh aspect of the present invention, the first pivot shaft is also a shaft for supporting the forceps member, it is possible to downsize the treatment portion more than the case in which a shaft for supporting and a shaft for rotating are provided separately, and so it is possible to reduce the number of components.

In the endoscope treatment tool in accordance with the eighth aspect of the present invention, the second pivot shaft is provided coaxially by one pair and so it is possible not to interrupt a field of view of an observation device when installed to the endoscope. Also, since the connection member is formed in a curved shape, it is possible to suppress an expansion of the outer shape thereof and so it is possible to facilitate the insertion into the body.

In accordance with the present invention, it is possible to assure an ideal endoscopic image for a case in which the submucosal layer is cut out by rotating the connection member and moving the treatment member. Therefore, it is possible to position the portion to be treated in an appropriate position and so the procedure becomes easy.

What is claimed is:

1. An endoscope treatment tool comprising: a cylindrical distal end member installed at the distal end of an endoscope, a treatment portion for performing a treatment relative to a biological tissue, an insertion portion provided so as to freely extend and retract in an axial line direction of the endoscope and the treatment portion is fixed at the outer circumference of the distal end thereof, a connection member for connecting both the treatment portion and the cylindrical distal end member in a freely rotatable manner, a first pivot shaft which is disposed on the distal end side of the treatment portion for connecting the connection portion and the treatment portion in a freely rotatable manner, a pair of second pivot shafts which are disposed on the distal end side of the distal end member and are formed along a diameter perpendicular to a longitudinal direction of the distal end member for connecting the connection member and the distal end member in a freely rotatable manner; wherein the connection member is curved so as to follow the outer shape of the distal end member; and the pair of second pivot shafts are disposed so as to be able to rotate the connection member so that the first pivot shaft is moved from a location which is proximal to the pair of second pivot shafts to a location which is distal to the pair of second pivot shafts.

2. The endoscope treatment tool in accordance with claim 1, wherein the connection member rotates when the insertion portion is extended and retracted relative to the endoscope, the first pivot shaft moves from a location proximal to the pair of second pivot shafts to a location distal to the pair of second pivot shafts when the insertion portion is extended relative to the endoscope.

3. The endoscope treatment tool in accordance with claim 2, wherein a distance between the treatment portion and the endoscope is maximum when the connection member rotates and the first pivot shaft and the pair of second pivot shafts are disposed on a plane that is substantially perpendicular to the longitudinal direction of the distal end member.

4. The endoscope treatment tool in accordance with claim 3, wherein the treatment portion projects from a distal end surface of the endoscope when the connection member rotates and the first pivot shaft moves to a location distal to the distal end surface of the distal end member.

5. The endoscope treatment tool in accordance with claim 3, wherein the treatment portion moves to a location beyond a center line of the distal end member when the connection member rotates and the first pivot shaft moves to a location distal to the distal end surface of the distal end member.

6. The endoscope treatment tool in accordance with any one of claim 1, and claim 2 to claim 5, wherein the treatment portion has such a constitution that a pair of forceps members is supported to a supporting member so as to be freely opened and closed, and each of the forceps members is supported by the supporting member and the first pivot shaft.

7. The endoscope treatment tool in accordance with claim 6, wherein
the pair of second pivot shafts are each coaxially inserted into a hole formed in the distal end member.

* * * * *